United States Patent [19]
Nakayama et al.

[11] Patent Number: 5,095,909
[45] Date of Patent: Mar. 17, 1992

[54] ULTRASOUND DIAGNOSTIC EQUIPMENT

[75] Inventors: Kiyoshi Nakayama, Koganei; Akira Shiba, Kawasaki, both of Japan

[73] Assignee: Fujitsu Limited, Kawasaki, Japan

[21] Appl. No.: 356,888

[22] Filed: May 25, 1989

[30] Foreign Application Priority Data

May 26, 1988 [JP] Japan .............................. 63-129073

[51] Int. Cl.$^5$ .............................................. A61B 8/00
[52] U.S. Cl. ................................. 128/660.06; 73/599
[58] Field of Search ..................... 128/660.06; 73/599, 73/602

[56] References Cited

U.S. PATENT DOCUMENTS

| | | | |
|---|---|---|---|
| 4,575,799 | 3/1986 | Miwa et al. | 128/660.06 X |
| 4,867,167 | 9/1989 | Magnin | 128/660.06 |

FOREIGN PATENT DOCUMENTS

| | | |
|---|---|---|
| EP-A-0064399 | 4/1982 | European Pat. Off. |
| EP-A-0349321 | 6/1990 | European Pat. Off. |

OTHER PUBLICATIONS

Shirou Miyagi et al. "In Vivo Tissue Characterization Using Blood Flow Doppler Signal as a Reference" J.S.U.M. BT, vol. 13-88, pp. 1-6.
Ophir, J. et al. "Attenuation Estimation in Reflection: Progress & Prospects", UTS Imaging 6, 349-395 (1984).
Parker, K. et al., "Measurement of UTS Attenuation Within Regions Selected from B-Scan Images", IEEE BME Transactions-30 #8. Aug. 1983, pp. 431–437.
The Japan Society of Ultrasonics in Medicine, Proceedings of the 52nd Meeting, Tokyo, Jun. 22-24, 1988. "In Vivo Tissue Characterization Using Blood Flow Doppler Signal as a Reference", Kiyoshi Nakayama and S. Yagi, pp. 399–400.

*Primary Examiner*—Francis Jaworski
*Attorney, Agent, or Firm*—Staas & Halsey

[57] ABSTRACT

Ultrasound diagnostic equipment for diagnosing a region of interest of an organ by using a scattering coefficient and an attenuation slope comprises a scattering power calculation unit for calculating a scattering spectrum of the region of interest, a cumulative attenuation slope calculation unit for calculating a cumulative attenuation slope of the intervening tissue between a body surface and a position of blood close to the region of interest by using a scattering coefficient of blood which is previously known, and a scattering coefficient calculation unit for calculating a scattering coefficient of the region of interest by using the calculated cumulative attenuation slope of the intervening tissue between body surface and the blood close to the region of interest. Therefore, a scattering coefficient and an attenuation slope of the region of interest can be calculated with high accuracy, and the region of interest can be exactly diagnosed by the calculated scattering coefficient and the attenuation slope thereof.

18 Claims, 8 Drawing Sheets

$t_1 = \frac{2D_1}{C}$ (where, a reference C denotes an acoustic velocity, a symbol $\langle \rangle$ denotes an average)

REAL COMPONENT OF QUADRATURE DETECTION

REAL COMPONENT OF DOPPLER SIGNAL

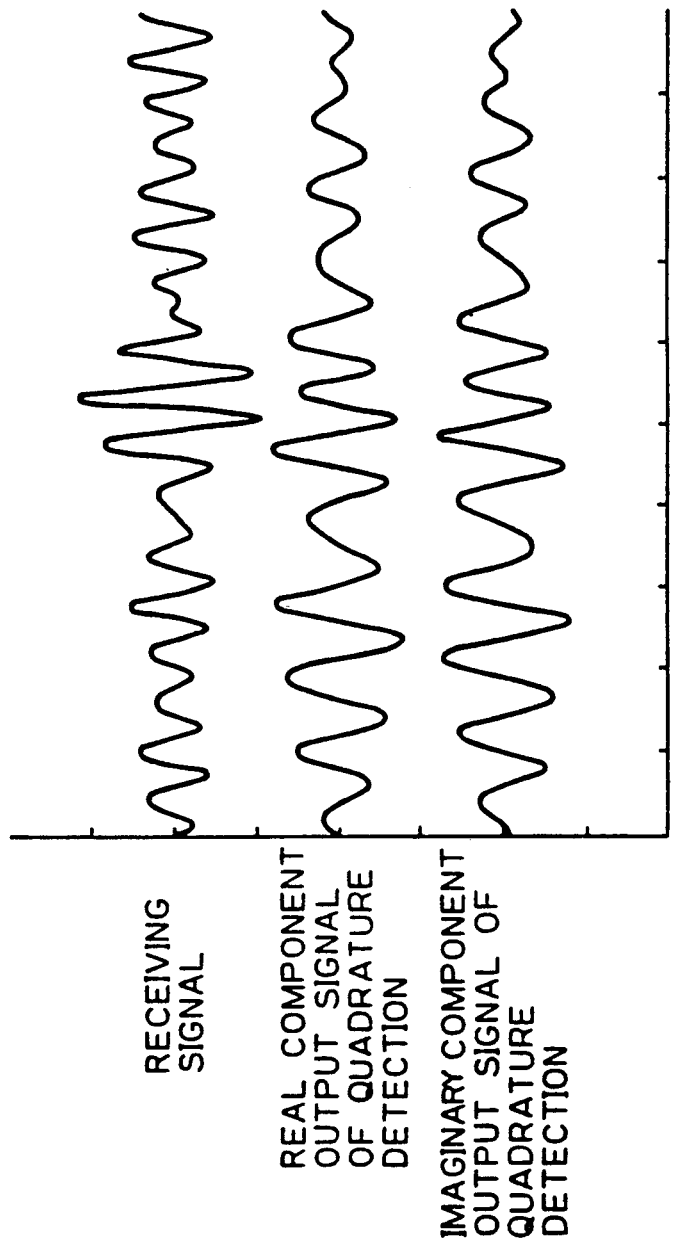

Fig. 7b
Fig. 7a
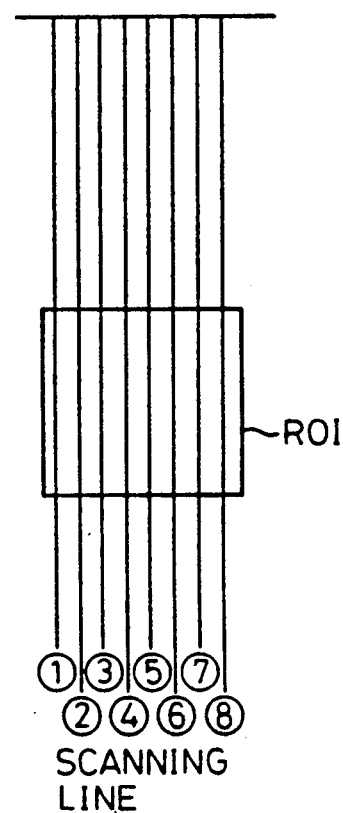
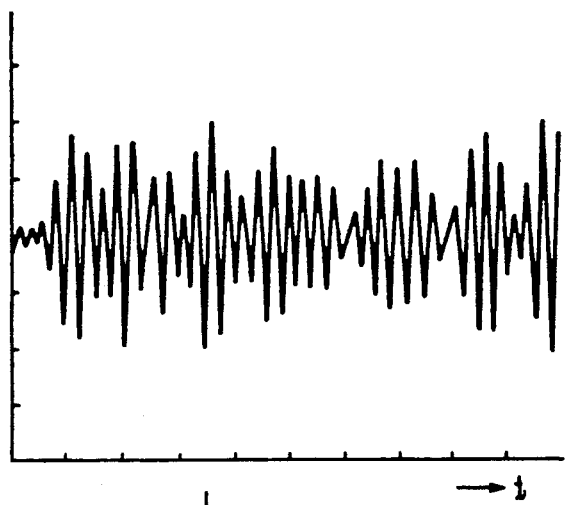
Fig. 7c
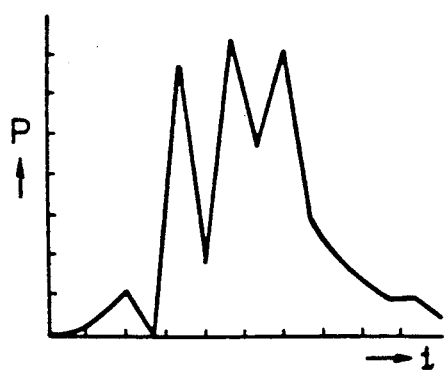
Fig. 7d
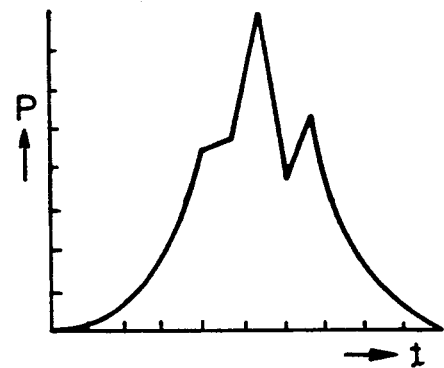
Fig. 7e
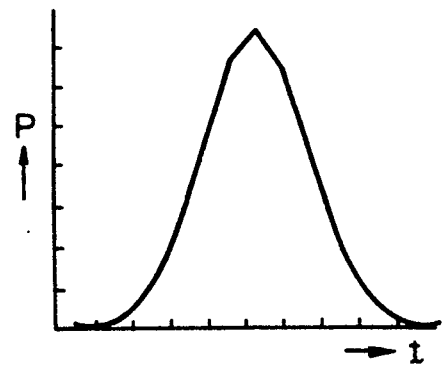

ULTRASOUND DIAGNOSTIC EQUIPMENT

BACKGROUND OF THE INVENTION

1. Field of the Invention

The present invention relates to ultrasound diagnostic equipment, more particularly, to ultrasound diagnostic equipment for diagnosing a region of interest of an organ by using a scattering coefficient and an attenuation slope of the region of interest.

2. Description of the Related Art

Recently, in accordance with progress in diagnostic techniques using an ultrasound wave, it has become necessary that diagnostic accuracy be improved by using diagnosis of acoustic characteristics of tissues, instead of a conventional diagnostic method for diagnosing from the shapes of internal organs or tumors. Now, acoustic characteristics of tissues, especially an attenuation coefficient (an attenuation slope) and a scattering coefficient (a differential scattering crosssection per unit volume), are used to indicate the characteristics of tissues. These coefficients are useful for detecting a diffuse disease and a cancer in a liver. The scattering coefficient is particularly useful for detecting a myocardial infarction. However, it is difficult to measure the above coefficients with high accuracy and to use these coefficients for practical diagnosis. Namely, when detecting an attenuation slope of the region of interest, a scattering coefficient thereof should be supposed to a specific fixed value, and conversely, when detecting a scattering coefficient of the region of interest, an attenuation slope thereof should be supposed to a specific fixed value.

Therefore, an accuracy of measurements of acoustic characteristics by radiating an ultrasound wave to an organ, receiving a scattered wave and calculating from the scattered wave, is not sufficient. Namely, it is difficult to determine the attenuation slope and the scattering coefficient exactly.

In a manner of speaking, the tissue of an organ is like gelatin including a plurality of particulates floating therein. Thus a power spectrum, a center frequency and an amplitude calculated by using a fast Fourier analysis of ultrasound scattered signals of one scanning line, have large stochastic variance. Therefore, acoustic characteristics calculated by using the power spectrum, the center frequency and the amplitude cannot have sufficient accuracy.

SUMMARY OF THE INVENTION

It is an object of the present invention to provide ultrasound diagnostic equipment for exactly diagnosing a region of interest of an organ using the calculated values of scattering coefficient and an attenuation slope of the region of interest. In the ultrasound diagnostic equipment of the present invention, flowing blood existing close to the region of interest is used as a standard reference target which has a specific value, since the scattering coefficient of blood does not fluctuate with individual differences.

According to the present invention, there is provided ultrasound diagnostic equipment for diagnosing a region of interest of an organ by using a scattering coefficient and/or an attenuation slope of the region of interest, which comprises a first ultrasound radiation and receipt unit and a cumulative attenuation slope calculation unit. The first ultrasound radiation and receipt unit is contacted to a body surface over an organ and is used for radiating an ultrasound beam to blood close to the region of interest and receiving an ultrasound wave scattered by the blood. The cumulative attenuation slope calculation unit is connected to the first ultrasound radiation and receipt unit and is used for calculating a cumulative attenuation slope of the intervening tissue between the body surface and a position of the blood.

The ultrasound diagnostic equipment may further comprise a coefficient calculation unit connected to the cumulative attenuation slope calculation unit, for calculating an average attenuation slope of the region of interest by using a plurality of cumulative attenuation slopes calculated by the cumulative attenuation slope calculation unit.

The ultrasound diagnostic equipment may further comprise a scattering coefficient calculation unit and a second ultrasound radiation and receipt unit. The scattering coefficient calculation unit is connected to the second ultrasound radiation and receipt unit, for calculating a scattering coefficient of the region of interest by using the calculated cumulative attenuation slope of the blood close to the region of interest. The second ultrasound radiation and receipt unit is contacted to the body surface over the organ for radiating an ultrasound beam to the region of interest and receiving an ultrasound wave scattered from the region of interest.

The second ultrasound radiation and receipt unit may comprise an ultrasound probe, a transmitting amplifier, and a receiving amplifier. The ultrasound probe is contacted to the body surface of the organ for radiating an ultrasound beam to an optional portion in the organ and receiving an ultrasound wave scattered from the optional portion. The transmitting amplifier is connected to the ultrasound probe for driving the ultrasound probe.

The receiving amplifier is connected to the ultrasound probe for amplifying the ultrasound wave signals received by the ultrasound probe. The scattering coefficient calculation unit may comprise a scattering spectrum calculation unit, a read only memory, and a coefficient calculation unit.

The scattering spectrum calculation unit may comprise an A/D converter, an operation circuit, a power operation circuit, and an accumulator. The A/D converter is connected to the receiving amplifier for converting an output signal of the receiving amplifier into a digital signal. The operation circuit is connected to the A/D converter for performing a high speed operation of a fast Fourier transform of an output signal of the A/D converter. The power operation circuit is connected to the operation circuit for calculating a real component and an imaginary component of the fast Fourier transform. The accumulator is connected to the power operation circuit for adding a power spectrum of a scanning line in the region of interest.

The scattering spectrum calculation unit may comprise a logarithmic amplifier, an A/D converter, an inverse logarithmic circuit, an arithmetic circuit, a power calculation circuit, and an accumulator. The A/D converter is connected the receiving amplifier, for amplifying the output signal of the receiving amplifier as a logarithmic compression. The A/D converter is connected to the logarithmic amplifier for converting an output signal of said logarithmic amplifier into a digital signal. The inverse logarithmic circuit is connected to the A/D converter for returning to a primary antilogarithm a output signal of the A/D converter. The arithmetic circuit is connected to the inverse logarithmic circuit for performing a high speed operation of a fast Fourier transform on an output signal of the inverse logarithmic circuit. The power calculation circuit is connected to the operation circuit for calculating a sum of a square of a real component and square of an imaginary component of the Fourier spectrum. The accumulator is connected to the power operation circuit, for adding a power spectrum of a scanning line in the region of interest.

The first ultrasound radiation and receipt unit may comprise an ultrasound probe contacted to the body surface over the organ and used for radiating an ultrasound beam to an optional portion in the organ and receiving an ultrasound wave scattered from the optional portion, a transmitting amplifier connected to the ultrasound probe and used for driving the ultrasound probe, and a receiving amplifier connected to the ultrasound probe and used for amplifying the ultrasound wave signals received by the ultrasound probe.

The cumulative attenuation slope calculation unit may comprise a scattering power calculation unit connected to the first ultrasound radiation and receipt unit and used for calculating an ultrasound scattering wave power scattered from the blood close to the region of interest by using a scattering coefficient of blood which is known to be constant, and a cumulative attenuation slope calculation unit connected to the scattering power calculation unit and used for calculating a cumulative attenuation slope based on an ultrasound scattering wave power calculated by the scattering power calculation unit.

The scattering power calculation unit may comprise a Doppler signal calculation circuit connected to the receiving amplifier and used for calculating a Doppler signal of the receiving amplifier in a sample volume, a power calculation circuit connected to the Doppler signal calculation circuit and used for calculating a power of the Doppler signal by calculating a sum and averaging in time the square of an imaginary component and the square of a real component of the Doppler signal, and an A/D converter connected to the power calculation circuit and used for converting the power of the Doppler signal into a digital signal.

The cumulative attenuation slope calculation unit may comprise a read only memory connected to the scattering power calculation unit, wherein transfer tables for the scattering power and depth to the cumulative attenuation slope calculated from the scattering coefficient of blood are memorized in the read only memory. diffraction characteristics of the ultrasound beam, transmitting-receiving characteristics, and a power transfer function including frequency characteristics of the equipment.

Further, the ultrasound diagnostic equipment may comprise a coefficient calculation unit connected to the cumulative attenuation slope calculation unit and used for calculating an average attenuation slope of an intervening tissue section among a plurality of blood positions based on the cumulative attenuation coefficients corresponding to the blood positions calculated by the cumulative attenuation slope calculation unit.

The coefficient calculation unit may calculate a scattering coefficient of the region of interest based on the calculated power spectrum of a reflected wave and the cumulative attenuation slope.

Furthermore, the ultrasound diagnostic equipment may comprise a B-mode receiving circuit connected to the receiving amplifier and used for generating a B-mode image using luminance signals corresponding to the signal strength of the output of the receiving amplifier.

According to the present invention, there is also provided ultrasound diagnostic equipment for diagnosing a region of interest of an organ by using a scattering coefficient and an attenuation slope of the region of interest, which comprises an ultrasound probe, a transmitting amplifier, a receiving amplifier, a timing control unit, a B-mode receiving circuit, a scattering spectrum calculation unit, a scattering power calculation unit, a cumulative attenuation slope calculation unit, a read only memory, a coefficient calculation unit, and a display. The ultrasound probe is contacted to a body surface over an organ and is used for radiating an ultrasound beam to an optional portion in the organ and receiving an ultrasound wave scattered from the optional portion. The transmitting amplifier is connected to the ultrasound probe. The receiving amplifier is connected to the ultrasound probe and is used for amplifying the ultrasound wave signal received by the ultrasound probe. The timing control unit is connected to the transmitting amplifier and is used for supplying pulse shape electrical signals to the transmitting amplifier. The B-mode receiving circuit is connected to the receiving amplifier and is used for generating a B-mode image using luminance signals corresponding to the signal strength of the output of the receiving amplifier. The scattering spectrum calculation unit is connected to the receiving amplifier and is used for calculating a scattering spectrum of the region of interest based on the output signals of the receiving amplifier. The scattering power calculation unit is connected to the receiving amplifier and the timing control unit and is used for calculating an ultrasound scattering wave power scattered from blood close to the region of interest and a timing signal output from the timing control unit. The cumulative attenuation slope calculation unit is connected to the scattering power calculation unit and the timing control unit and is used for calculating a cumulative attenuation slope based on a ultrasound scattering wave power calculated by the scattering power calculation unit and the timing signal output from the timing control unit. The read only memory is connected to the timing unit and is used for reading out various data in response to addresses from the timing control unit. The coefficient calculation unit is connected to the scattering spectrum calculation unit, the cumulative attenuation slope calculation unit and the read only memory and is used for calculating a scattering coefficient of the region of interest and an attenuation slope of an intervening tissue between two blood positions. The display is connected to the B-mode receiving circuit and the coefficient calculation unit and is used for displaying a B-mode image and an image characterized by the scattering coefficient of the region of interest and the attenuation slope of an intervening tissue between blood position.

The scattering spectrum calculation unit may comprise an A/D converter connected to the receiving amplifier and used for converting an output signal of the receiving amplifier into a digital signal, an operation circuit connected to the A/D converter and used for performing a high speed operation of a fast Fourier transform of an output signal of the A/D converter, a power operation circuit connected to the operation circuit and used for calculating a real component and an imaginary component of the Fourier spectrum, and an accumulator connected to the power operation circuit and used for adding a power spectrum of a scanning line in the region of interest.

The scattering spectrum calculation unit may comprise a logarithmic amplifier connected to the receiving amplifier and used for amplifying the output signal of the receiving amplifier as a logarithmic compression, an A/D converter connected to the logarithmic amplifier and used for converting an output signal of the logarithmic amplifier into a digital signal, an inverse logarithmic circuit connected to the A/D converter and used for returning to a primary antilogarithm output signal of the A/D converter, an operation circuit connected to the inverse logarithmic circuit and used for performing a high speed operation of a fast Fourier transform of an output signal of the inverse logarithmic circuit, a power calculation circuit connected to the operation circuit and used for calculating a real component and an imaginary component of the Fourier spectrum, and an accumulator connected to the power operation circuit and used for adding a power spectrum of a scanning line in the region of interest.

The scattering power calculation unit may comprise a Doppler signal calculation circuit connected to the receiving amplifier and the timing control unit and used for calculating a Doppler signal of the receiving amplifier in a sample volume by the timing signal from the timing control unit, a power calculation circuit connected to the Doppler signal calculation circuit and used for calculating a power of the Doppler signal by calculating a sum and averaging in time of the square of an imaginary component and the square of a real component of the Doppler signal, and an A/D converter connected to the power calculation circuit and used for converting the power of the Doppler signal into a digital signal.

The cumulative attenuation slope calculation unit may comprise a read only memory connected to the scattering power calculation unit and the timing control unit, wherein scattering characteristics of the ultrasound beam, transmitting-receiving characteristics, and a power transfer function including frequency characteristics of the equipment are stored in the read only memory.

BRIEF DESCRIPTION OF THE DRAWINGS

The present invention will be more clearly understood from the description of the preferred embodiments as set forth below with reference to the accompanying drawings, wherein:

FIG. 6c output signal of guad rature detector; and

FIGS. 7a to 7e are explanatory diagrams of a power spectrum of a reflected wave.

DESCRIPTION OF THE PREFERRED EMBODIMENTS

The principle of the present invention will be explained, before explanation of an embodiment.

Ultrasound diagnostic equipment of the present invention diagnoses a region of interest ROI of an organ by using a scattering coefficient of the region of interest ROI and an attenuation slope of the intervening tissue between two blood portions by an ultrasonic Tissue Characterization (TC).

First, an ultrasound beam UB is radiated from an ultrasound probe through a body surface BS to blood which is positioned close to the region of interest ROI. An ultrasound wave scattered from the blood is received by the ultrasound probe. That is, a region of interest ROI is located close to a blood vessel where a scattered power spectrum of the received ultrasound wave signals can be provided. Further, a cumulative attenuation slope between the body surface BS and the position of the blood is calculated by using a scattering coefficient of blood. Note, the scattering coefficient of the blood can be known previously, and does not fluctuate at each position of a human body or by individual difference.

Next, an ultrasound beam UB is radiated from an ultrasound probe through a body surface BS to a region of interest ROI. An ultrasound wave scattered from the region of interest ROI is received by the ultrasound probe. Further, a scattering coefficient of the region of interest ROI is calculated by using the cumulative attenuation slope of the intervening tissue between the body surface and the blood close to the region of interest ROI. Note, the measurement position of the blood is not only a position of a blood vessel, but also a position of existing blood, i.e., a heart, and the like.

Next, an embodiment of ultrasound diagnostic equipment of the present invention will be explained with reference to the drawings.

Figure 1:
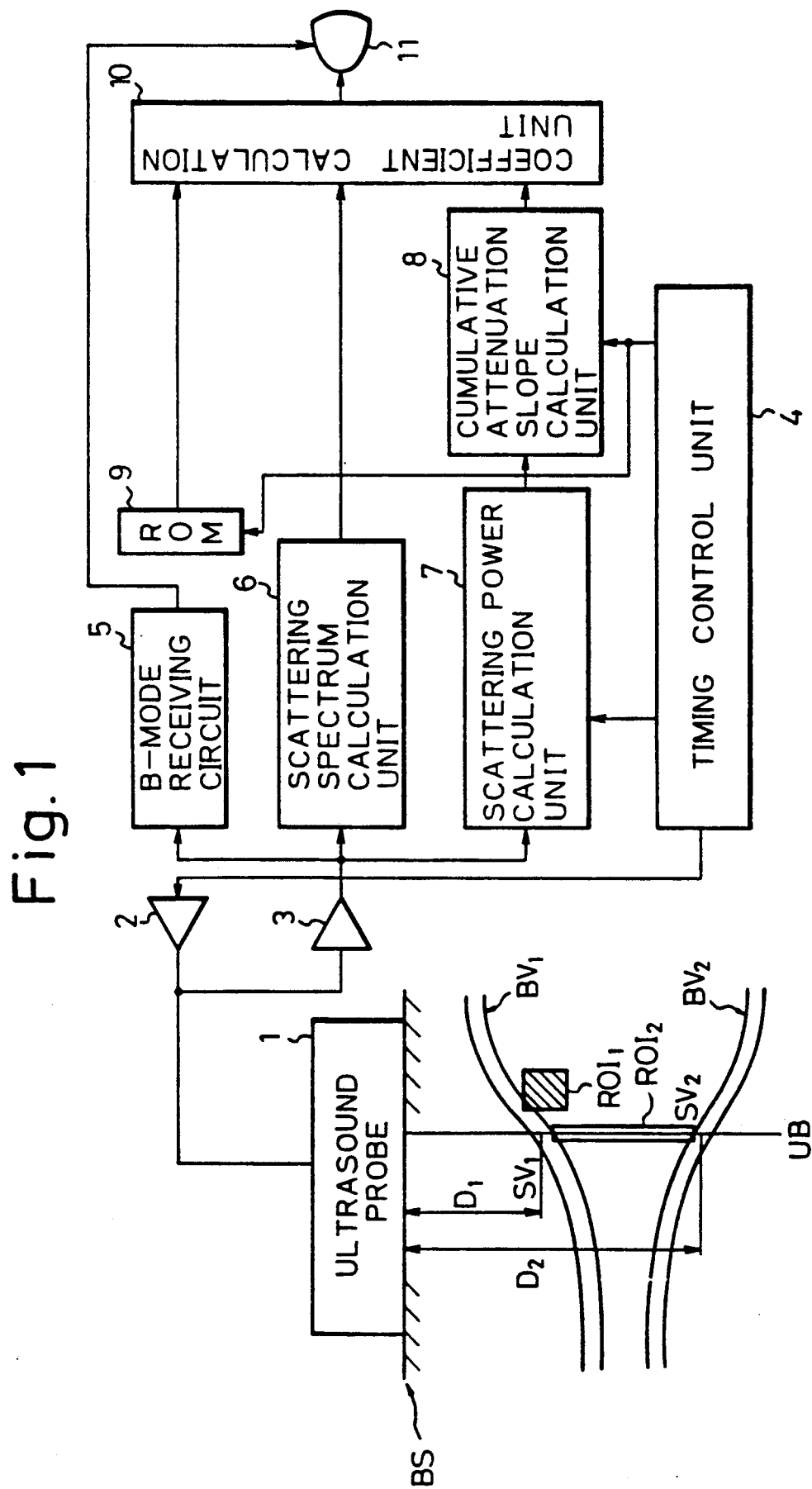
FIG. 1 is a block diagram showing a construction of an embodiment of ultrasound diagnostic equipment according to the present invention.

FIG. 1 is a block diagram showing a construction of an embodiment of ultrasound diagnostic equipment according to the present invention. As shown in FIG. 1, ultrasound diagnostic equipment is used for diagnosing a region of interest ROI of an organ by using a scattering coefficient of the region of interest ROI and an attenuation slope of the intervening tissue. The ultrasound diagnostic equipment comprises an ultrasound probe 1, a transmitting amplifier 2, a receiving amplifier 3, a timing control unit 4, a B-mode receiving circuit 5, a scattering spectrum calculation unit 6, a scattering power calculation unit 7, a cumulative attenuation slope calculation unit 8, a read only memory 9, a coefficient calculation unit 10, and a display 11.

The ultrasound probe 1 is contacted to a body surface BS over the organ and used for radiating an ultrasound beam UB to an optional portion in the organ and receiving an ultrasound wave scattered from the optional portion. Note, the optional portion is, for example, a position $SV_1$ of blood in blood vessel $BV_1$ or a position $SV_2$ of blood in blood vessel $BV_2$. These positions $SV_1$ and $SV_2$ are located close to the region of interest ROI.

The transmitting amplifier 2 is connected to the ultrasound probe 1 and used for driving the ultrasound probe 1 by inputting pulse shape electrical signals thereto. The receiving amplifier 3 is connected to the ultrasound probe 1 and used for amplifying the ultrasound wave signals received by the ultrasound probe 1.

The timing control unit 4 is connected to the transmitting amplifier 2 and used for supplying pulse shape electric signals to the transmitting amplifier 2.

The B-mode receiving circuit 5 is connected to the receiving amplifier 3 and used for generating a B-mode image using luminance signals corresponding to the signal strength of the output of the receiving amplifier 3.

The scattering spectrum calculation unit 6 is connected to the receiving amplifier 3 and used for calculating a scattering spectrum of the region of interest ROI by the output signals of the receiving amplifier 3.

The scattering power calculation unit 7 is connected to the receiving amplifier 3 and the timing control unit 4, and used for calculating an ultrasound scattering wave power $P(D_i)$ scattered from the blood close to the region of interest ROI and a timing signal output from the timing control unit 4.

The cumulative attenuation slope calculation unit 8 is connected to the scattering power calculation unit 7 and the timing control unit 4, and used for calculating a cumulative attenuation slope based on the ultrasound scattering wave power $P(D_i)$ calculated by the scattering power calculation unit 7 and the timing signal output from the timing control unit 4.

The read only memory (ROM) 9 is connected to the timing control unit 4, and used for reading out various data in response to addresses from the timing control unit 4. Note, the data stored in the ROM 9 is, for example, diffraction characteristics of the ultrasound beam, transmit and receive characteristics, and power transfer functions including frequency characteristics of the ultrasound diagnostic equipment.

The coefficient calculation unit 10 is connected to the scattering spectrum calculation unit 6, the cumulative attenuation slope calculation unit 8 and the read only memory 9, and used for calculating a scattering coefficient of the region of interest ROI by the power spectrum of scattered wave from the region of interest ROI 1, and cumulative attenuation slopes, and used for calculating an attenuation slope of the region of interest ROI 2 by a plurality of commutative attenuation slopes.

A coefficient calculation unit 10 is used for calculating an average attenuation coefficient, a scattered coefficient, and the like.

The display 11 is connected to the B-mode receiving circuit 5 and the coefficient calculation unit 10, and used for displaying a B-mode image and an image characterized by the scattering coefficient of the region of interest ROI and the attenuation slope.

As shown in FIG. 1, the scattering power calculation unit 7 calculates an ultrasound scattering wave power $P(D_i)$ by using received signals scattered by blood in a blood vessel which has definite scattering characteristics. The cumulative attenuation slope calculation unit 8 calculates a cumulative attenuation slope by using the ultrasound scattering wave power $(D_i)$ and an average attenuation slope by using a plurality of cumulative attenuation coefficients with high accuracy.

Further, the scattering spectrum calculation unit 6 calculates ultrasound scattering wave power spectrums of a plurality of signals scattered by a region of interest ROI 1, and the coefficient calculation unit 10 calculates a scattering coefficient and an attenuation slope by using the ultrasound scattering wave power spectrums of a plurality of signals with high accuracy.

Therefore, coefficients (a cumulative attenuation slope and an average attenuation slope) of an organ can be calculated with high accuracy based on the signals scattered by blood having definite scattering characteristics. Further, a scattering coefficient of a region of interest ROI 1 located close to a blood vessel can be calculated with high accuracy by using the above cumulative attenuation slope of the intervening tissue between the body surface and the blood.

Next, an operation of the ultrasound diagnostic equipment shown in FIG. 1 will be explained.

First, the ultrasound diagnostic equipment is adjusted so that an ultrasound scattering wave power of a receiving signal scattered from a position $SV_1$ of blood in a blood vessel $BV_1$ can be calculated. Next, an ultrasound wave at a position of an ultrasound beam UB is received many times, and receiving signals scattered from the position $SV_1$ are calculated as an average-sum, so that an ultrasound scattering wave power $P(D_i)$ is calculated by a scattering power calculation unit 10. Note, scattering characteristics of blood have only slight deviation in different human bodies, and thus the scattering characteristics of the blood can be determined as a standard coefficient. Further, the ultrasound scattering wavepower $P(D_i)$ of blood is proportional to the 4th power of frequency $f_\phi$, and an attenuation slope of an organ is equal to the frequency $f_0$. Below, calculations of the cumulative attenuation slope, the average attenuation slope, and the scattering coefficient are explained in detail.

An attenuation slope at a position of a depth z from a body surface BS $\beta$ (z) (dB/MHz/cm), a turn around cumulative attenuation slope $B_1$ (dB/MHz) and a cumulative attenuation (dB) are indicated by the following equations (1) and (2).

$$B_1 = 2\int_0^{D_1\beta} (x)dx(dB/MHz) \quad (1)$$

Cumulative attenuation $= B_1 \lfloor f \rfloor (dB)$ (2)

Assuming that power transfer characteristics including scattering characteristics and transmit receive characteristics of an ultrasound beam UB is a distance $D_1$ from the body surface BS to a measurement point $SV_1$ of a scattering power and frequency characteristics of the equipment, a received power spectrum $R(f, D_1)$ from the measurement point $SV_i$ of the scattering power is indicated by the following equation (3).

$$R(f,D_1) = G(f,D_1) \cdot B_0f^4 \cdot 10^{-B_1\lfloor f \rfloor/10} \quad (3)$$

Where, $B_0f^4$ indicates a scattering coefficient of blood which value is previously known.

Therefore, an ultrasound scattering wave power (a receiving power) $P(D_1)$ scattered by a measurement point $SV_1$ is indicated by the following equation (4).

$$P(D_1) \overset{\cdot}{=} \int_{-\infty}^{+\infty} R(f, D_1) df \qquad (4)$$

$$= \int_{-\infty}^{-\infty} G(f, D_1) \cdot b_0^A \cdot 10^{-B_1|f|/10} df$$

Note, a sensitivity of a standard ultrasound probe has been calibrated by using a small sphere of tungsten carbide positioned sufficiently far from the standard ultrasound probe, a scattering coefficient in a floating solution including fine grains of a dextran have been absolutely measured by the calibrated standard ultrasound probe, the floating solution of the fine grains is determined as a standard phantom, and a value of $G(f, D_1)$ is obtained by measuring a scattering power spectrum from a depth $D_1$ using the ultrasound probe and the ultrasound diagnostic equipment. Therefore, if the cumulative attenuation slope $B_1$ is given, a receiving power $P(D_1)$ corresponding to the depth $D_1$ can be calculated by using the equation (4). Since the ultrasound scattering wave power $P(D_1)$ and cumulative attenuation slope $B_1$ are single-valued functions the cumulative attenuation slope $B_1$ can also be easily calculated by using the depth $D_1$ and the ultrasound scattering wave power $P(D_1)$.

Consequently, a cumulative attenuation slope $B_1$ can be obtained from an ultrasound scattering wave power $P(D_1)$ by previously stored data in a ROM 8 in FIG. 1. That is, the cumulative attenuation slope $B_1$ can be obtained by a scattering power calculation unit 8 in FIG. 1. Further, a cumulative attenuation slope $B_1$ can be obtained by inputting a depth $D_1$ and an ultrasound scattering wave power $P(D_1)$ to the equation (4). Similarly, an ultrasound scattering wave power $P(D_2)$ at a measuring point $SV_2$ can be obtained. An average attenuation slope $\beta_{12}$ (dB/MHz/cm) of the region of interest $ROI_2$ among the measuring points $SV_1$ and $SV_2$ is calculated. That is, the average attenuation slope is calculated by a coefficient calculation unit 10 in FIG. 1 by the following equation (5).

$$\beta_{12} = (B_1 - B_2) / 2(D_2 - D_1) \qquad (5)$$

Further, an average power spectrum $R_{ROI(f)}$ of receiving signals from a region of interest ROI close to the measuring point $SV_1$ of the scattering power is obtained by the following equation (6).

$$R_{ROI(f)} = G(f, D_1) \cdot S(f) \cdot 10^{-B_1|f|/10} \qquad (6)$$

Where, S(f) indicates scattering characteristics of the region of interest ROI. Note, a value or the cumulative attenuation slope $B_1$ is previously obtained, and thus S(f) is calculated by the following equation (7).

$$S(f) = R_{ROI}(f) / (G(f, D_1) \cdot 10^{-B_1|f|/10}) \qquad (7)$$

Figure 2:
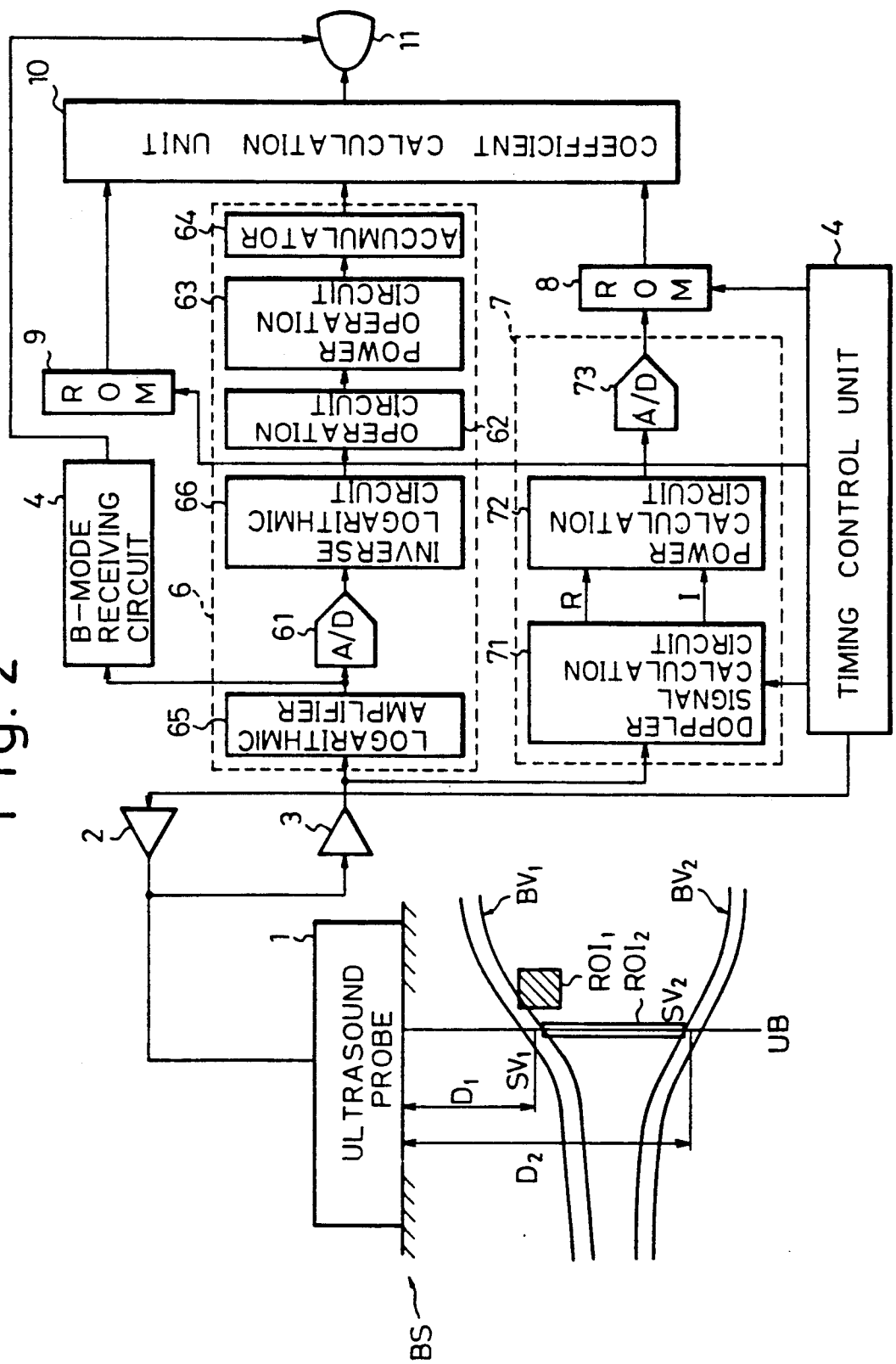
FIG. 2 is a block diagram showing one example of the ultrasound diagnostic equipment shown in FIG. 1.

Next, a construction of FIG. 2 will be explained. FIG. 2 is a block diagram showing one example of the ultrasound diagnostic equipment shown in FIG. 1.

As shown in FIG. 2, the scattering spectrum calculation unit 6 comprises a logarithmic amplifier 65, an A/D converter 61, an inverse logarithmic circuit 66, an operation circuit 62, a power operation circuit 63, and an accumulator 64.

The logarithmic amplifier 65 is connected to the receiving amplifier 3, and used for amplifying an amplitude of the output signal of the receiving amplifier 3 as a logarithmic compression. The A/D converter 61 is connected to the logarithmic amplifier 65, and used for converting an output signal of the logarithmic amplifier 65 into a digital signal. The inverse logarithmic circuit 66 is connected to the A/D converter 61, and used for returning to an output signal of the A/D converter 61 to a primary antilogarithm. The arithmetic circuit 62 is connected to the inverse logarithmic circuit 66 and used for performing a high speed calculation of a Fourier spectrum of an output signal of the inverse logarithmic circuit 66. The power calculation circuit 63, is connected to the operation circuit 62, and used for calculating a sum of the square of a real component and the square of an imaginary component of the fast Fourier transform. The accumulator 64 is connected to the power operation circuit 63 and used for adding a power spectrum of a scanning line in the region of interest ROI.

The scattering power calculation unit 7 comprises a Doppler signal calculation circuit 71, a power calculation circuit 72, and an A/D converter 73. The Doppler signal calculation circuit 71 is connected to the receiving amplifier 3 and the timing control unit 4 and used for calculating a Doppler signal of the receiving amplifier 3 in a sample volume by the timing signal from the timing control unit 4. The power calculation circuit 72 is connected to the Doppler signal calculation circuit 71, and used for calculating power of the Doppler signal by calculating a sum of a square and averaging in time between an imaginary component and a real component of the Doppler signal. The A/D converter 73 is connected to the power calculation circuit 72 and used for converting the power of the Doppler signal into a digital signal.

The cumulative attenuation slope calculation unit 8 comprises a read only memory which is connected to the scattering power calculation unit 7 and the timing control unit 4. Note, transfer tables from the scattering powder $P(D_1)$ and depth $D_1$ to the cumulative attenuation slope are stored in the read only memory 8, which are calculated from the scattering coefficient of blood, diffraction characteristics of the ultrasound beam UB, transmitting-receiving characteristics, and a power transfer function including frequency characteristics of the equipment.

Figure 3:
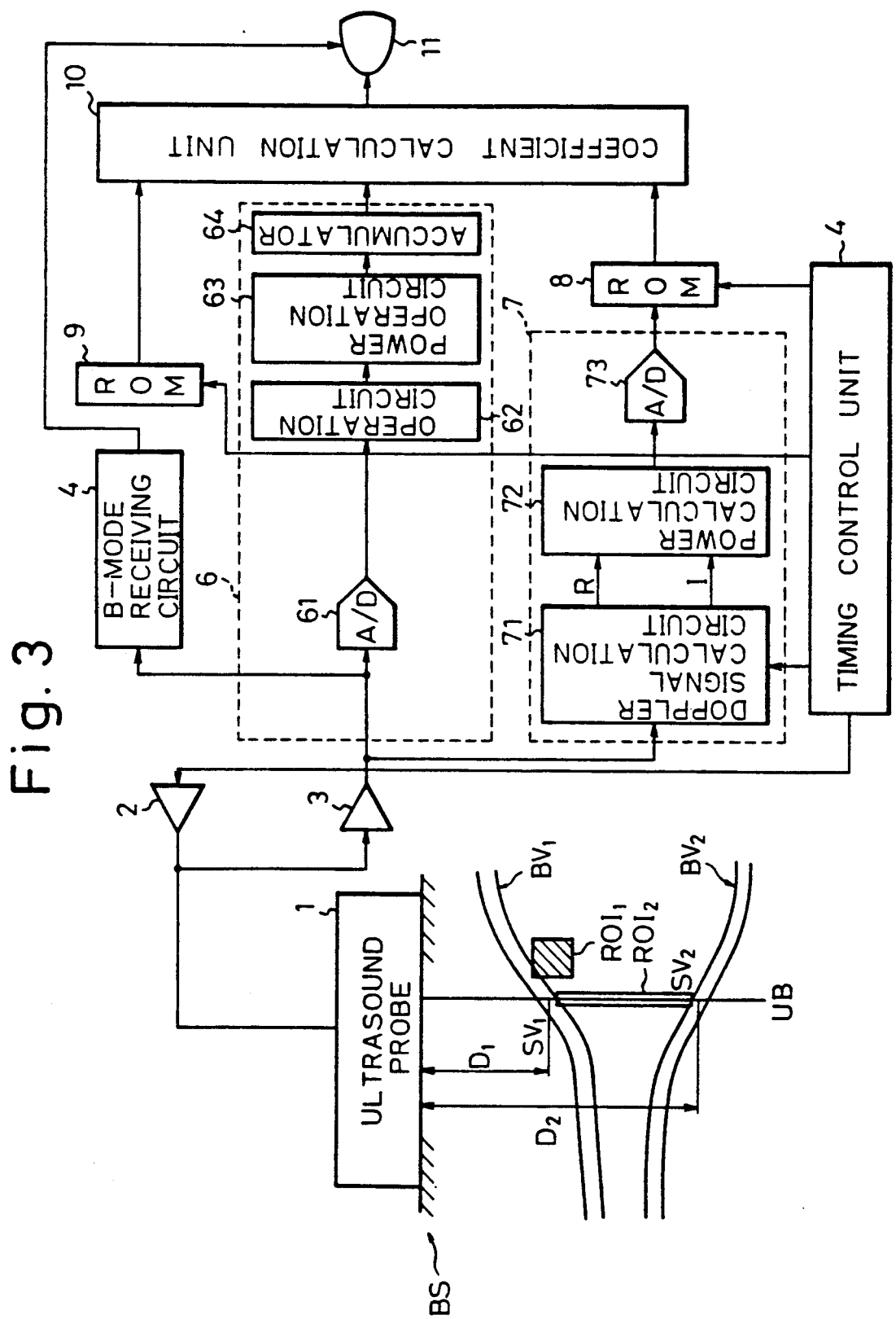
FIG. 3 is a block diagram showing another example of the ultrasound diagnostic equipment shown in FIG. 1.

FIG. 3 is a block diagram showing another example of the ultrasound diagnostic equipment shown in FIG. 1. This ultrasound diagnostic equipment of FIG. 3 does not include a logarithmic amplifier 65 and an inverse logarithmic circuit 66 shown in FIG. 2. The logarithmic amplifier 65 and the inverse logarithmic circuit 66 are used for improving dynamic range of digital output data, and thus the logarithmic amplifier 65 and inverse logarithmic circuit 66 are not always necessary.

Next, an operation of the construction of FIG. 2 including the construction of FIG. 3 will be explained.

In FIG. 2, an ultrasound wave UB is radiated from the ultrasound probe 1 to an organ by pulse signals output from the transmitting amplifier 2. An ultrasound wave is scattered and returned from the organ in sequence. An ultrasound scattering signal received by the ultrasound probe 1 is amplified by the receiving amplifier 3. The amplified receiving signal is processed through the logarithmic amplifier 65 of the scattering spectrum calculation unit 6. The amplified receiving signal is also processed through the B-mode receiver, and then a B-mode image is displayed on the display unit 11.

Further, in order to obtain a cumulative attenuation slope, the Doppler signal calculation circuit 71 outputs a Doppler signal based on a receiving signal scattered from the sample volume $SV_1$ of blood vessel $BV_1$. The power calculation circuit 72 calculates a power of the Doppler signal, and the A/D converter 73 converts an output signal of the power calculation circuit 72 to a digital value. The ROM 8 outputs a cumulative attenuation slope, i.e., a cumulative attenuation slope $B_1$ from a body surface BS to a position of the sample volume $SV_1$, corresponding to the digital value. Similarly, a cumulative attenuation slope $B_2$ from the body surface BS to the sample volume $SV_2$ is calculated. The coefficient calculation unit 10, which receives the cumulative attenuation slope $B_1$ and the cumulative attenuation slope $B_2$, calculates an average attenuation slope from the sample volume $SV_1$ to the sample volume $SV_2$.

Further, in order to calculate a scattering coefficient of the region of interest ROI close to the blood vessel $BV_1$, a logarithmic amplifier 65 compresses logarithmically a receiving signal, and the A/D converter 61 converts an output signal to a digital value. Furthermore, the inverse logarithmic circuit 66 returns an output of the A/D converter 61 to a primary value. The operation circuit 62, which is a Fast Fourier Transform operation circuit, performs a Fourier analysis of RF data of a receiving signal from the region of interest ROI, and the power operation circuit 63 calculates a power spectrum from an output signal of the operation circuit 62. The accumulator 64 sums up and averages the power spectrum of each scanning line, and generates an average power spectrum. The coefficient calculation unit 10 calculates scattering characteristics S(f) of tissues in the region of interest ROI by using the average power spectrum RROI (f) and the cumulative attenuation slope $B_1$ of the blood vessel $BV_1$ output from the ROM 8, and substituting diffraction characteristics of an ultrasound beam output from the ROM 9, transmitting receiving characteristics, power transfer function G(f, x) including frequency characteristics of the equipment, a distance from the body surface BS to the region of interest ROI and the like, into the equation (5) and the like.

Next, concepts and operations of the Doppler signal calculation circuit 71 and the power calculation circuit 72 will be described.

Figure 4:
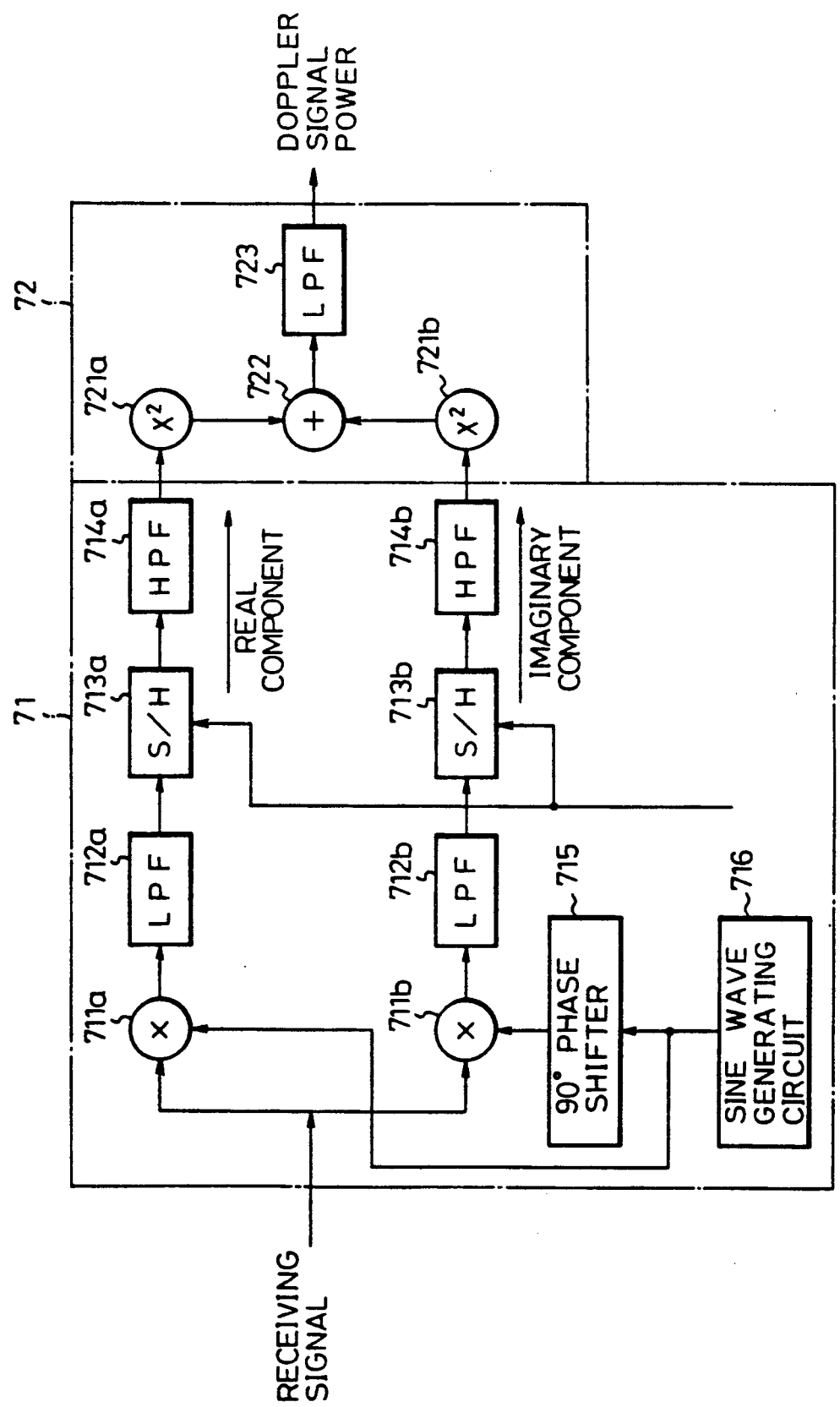
FIG. 4 is a circuit block diagram showing an example of a scattering power calculation unit of ultrasound diagnostic equipment according to the present invention.

FIG. 4 is a circuit block diagram showing an example of a scattering power calculation unit of ultrasound diagnostic equipment according to the present invention, and this drawing is a concrete example of the Doppler signal calculation circuit 71 and the power calculation circuit 72 in FIGS. 2 and 3. As shown in FIG. 4, the Doppler signal calculation circuit 71 comprises pairs of multipliers 711a and 711b, low pass filters (LPF) 712a and 712b, sample hold circuits (S/H) 713a and 713b and high pass filters (HPF) 714a and 714b. Further, the Doppler signal calculation circuit 71 comprises a phase shifter 715 and a sine wave generating circuit 716. The power calculation circuit 72 comprises a pair of squaring units 721a and 721b, an adder 722, and a low pass filter (LPF) 723.

In FIG. 4, receiving signals amplified by the receiving amplifier 3 are input to the multipliers 711a and 711b, respectively. Frequency signals f output from the sine-wave generating circuit 716 are supplied to the adder 711a and the phase shifter 715. The frequency signal f is shifted by 90 degrees by the phase shifter 715, and the shifter frequency signal is supplied to the adder 711b.

Output signals of the adders 711a and 711b are supplied to the sample hold circuits 713a and 713b through the low pass filters 712a and 712b. A real component of a Doppler signal is sampled and held by the sample hold circuit 713a, and an imaginary component of the Doppler signal is sampled and held by the sample hold circuit 713b. Note, high-frequency components of output signals of the multipliers 711a and 711b are eliminated by each of the low pass filters 712a and 712b.

Output signals of the sample hold circuits 713a and 713b are supplied to the high pass filters 714a and 714b, and low-frequency factors of the real component and the imaginary component of the Doppler signal are eliminated by each of the high pass filters 714a and 714b. Therefore, the real component and the imaginary component of the Doppler signal can be brought out.

These brought-out real components and imaginary components of the Doppler signal are squared by the squaring units 721a and 721b in the power calculation circuit 72, and added by the adder 722. Further, high-frequency components of an output signal of the adder 722 are eliminated by the low pass filter 723, and power of the Doppler signal or an ultrasound scattering wave power $P(D_1)$ is calculated. Similarly, referring to a sample volume $SV_2$, an ultrasound scattering wave power $P(D_2)$ is calculated.

In addition, referring to these calculated ultrasound scattering wave powers $P(D_1)$ and $P(D_2)$, they are converted into digital values by passing them through A/D converter 73 shown in FIGS. 2 and 3. The converted digital signals and the depth values $D_1$ and $D_2$ are input to the ROM 8 as its address signals, and cumulative attenuation slopes $B_1$ and $B_2$ are output as its output data which is then transferred to a coefficient calculation unit 10.

As described above, ultrasound scattering wave powers $P(D_1)$ and $P(D_2)$ of Doppler signals are calculated from receiving signals which are scattered from red blood cells having scattering coefficients with small individual differences, cumulative attenuation slopes $B_1$ and $B_2$ are calculated by using a ROM 8, and thus an average attenuation slope of the region of interest ROI 2 can be calculated with high accuracy.

Figure 5A:
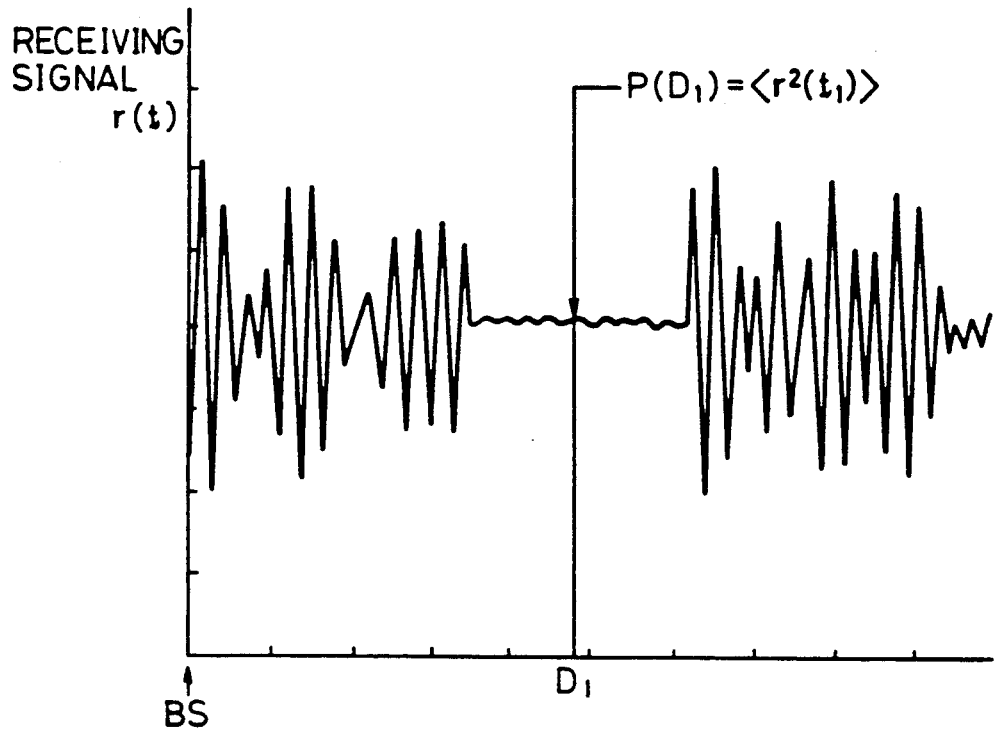
FIGS. 5a and 5b are explanatory diagrams for explaining calculation of an ultrasound scattering wave power scattered from blood.
Figure 5B:
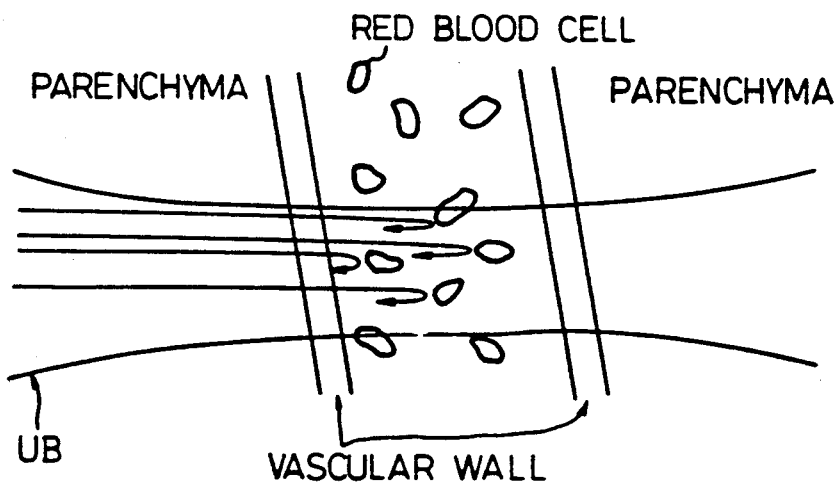

FIGS. 5a and 5b are explanatory diagrams for explaining the calculation of an ultrasound scattering wave power scattered from blood. and FIG. 5a indicates a receiving signal and FIG. 5b indicates the situation in which an ultrasound wave is scattered by blood corresponding to each blood vessel.

As shown in FIG. 5b, when an ultrasound beam enters into blood flowing in a blood vessel, the ultrasound beam UB is scattered by the red blood cells, and the scattered ultrasound wave is received by the ultrasound probe 1, and an ultrasound scattering wave power $P(D_1)$ is output as described above. It was clarified by experimentation by the present inventors that a scattering coefficient which indicates the extent of scattering has very small fluctuations regardless of individual differences. Consequently, a cumulative attenuation slope of a position of the blood vessel can be calculated with high accuracy by an ultrasound scattering wave power $P(D_1)$. Note, an average value of the ultrasound scattering wave power at the distance $D_1$ is indicated by $<r^2(t_1)>$, and thus the ultrasound scattering wave power $P(D_1)$ is indicated by the following equation.

$$P(D_1) = <r^2(t_1)>, \quad t_1 = 2D_1/C$$

Where, reference C denotes an acoustic velocity in a human body.

Figure 6A:
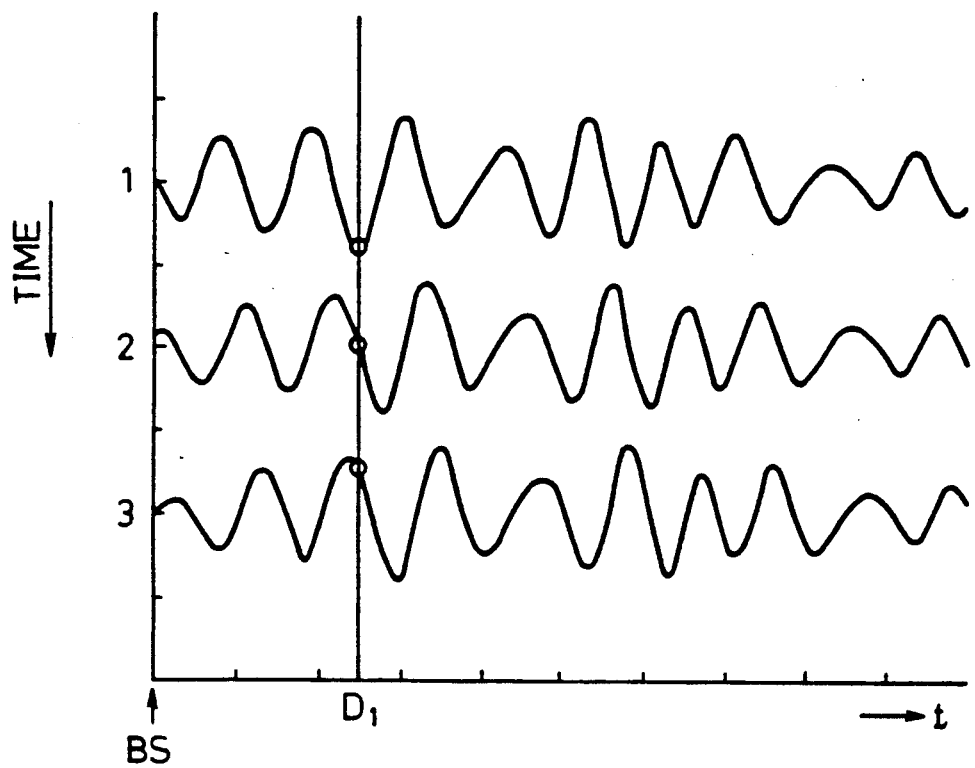
FIG. 6a is an explanatory diagram of a real component of an quadrature detection.

FIG. 6a is an explanatory diagram of a real component of an guadrature detection, and indicates real components of a detected receiving signal. These real components correspond to real components of the Doppler signals calculation by the Doppler signal calculate circuit 71 in FIGS. 2 and 3.

Figure 6B:
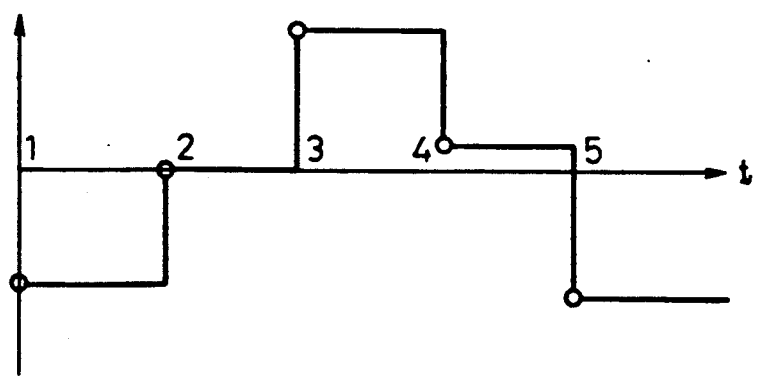
FIG. 6b is an explanatory diagram of a real component of a Doppler signal.

FIG. 6b is an explanatory diagram of a real component of a Doppler signal, which indicates real components Doppler signals, and shows time variation by of the points marked with circles in FIG. 6a.

FIG. 6c is an explanatory diagram of a Doppler signal, and indicates a quadrature detection output of real components and an orthogonal detection output of imaginary components calculated from receiving signals by the Doppler signal calculation circuit 71. These real components and imaginary components are output as denoted by R and I by the Doppler circuit 71 in FIGS. 2 and 3.

Next, an operation for calculating a scattering coefficient in the region of interest ROI with high accuracy will be explained with reference to FIGS. 7a to 7e.

FIG. 7a indicates a situation in which the region of interest ROI is scanned by scanning lines 1 and 2.

FIG. 7b indicates a wave-form of a receiving signal by the scanning line 1.

FIG. 7c indicates an ultrasound power spectrum in the region of interest ROI calculated from the receiving wave form of the scanning line 1. The curve is irregular and is not very accurate because it is calculated by a power operation circuit 63 (FIGS. 2 and 3) which operates for only one scanning line 1.

FIG. 7d indicates an average of the power spectrums of 1 and 2 in FIG. 7a. In this way, irregularities included in the power spectrums are decreased and a precision thereof can be increased.

FIG. 7e indicates an average of the power spectrums when a size of the region of interest ROI is determined to be much larger and a plurality of power spectra of scanning lines are used. In these power spectra, the curve is not irregular and the precision thereof is increased and has higher accuracy.

Consequently, when a size of the region of interest ROI is determined to be about 1 cm×1 cm, scanning lines are determined to be much greater, and a plurality of averages are calculated by the accumulator 64 in FIGS. 2 and 3, an ultrasound power scattering spectrum having high accuracy is calculated. Therefore, a scattering coefficient of the region of interest ROI can be calculated with high accuracy by the coefficient calculation unit 10 in FIGS. 2 and 3 based on the ultrasound scattering wave power spectrum of the region of interest ROI calculated with high accuracy and the previously calculated cumulative attenuation slope B1 and the like.

According to the present invention as in the above descriptions, attenuation coefficients (an average attenuation slope) are calculated based on signals scattered by blood in a blood vessel and are received having definite scattering characteristics. A scattering coefficient of a region of interest ROI 1 are calculated by using the cumulative attenuation slope and averaging a plurality of ultrasound power spectrum of the region of interest ROI 1. Thus the attenuation slopes (the cumulative attenuation slope and the average attenuation slope) and the scattering coefficient of the region of interest can be calculated with high accuracy.

Many widely different embodiments of the present invention may be constructed without departing from the spirit and scope of the present invention, and it should be understood that the present invention is not limited to the specific embodiments described in this specification, except as defined in the appended claims.

We claim:

1. Ultrasound diagnostic equipment for diagnosing a region of interest of an organ of a body by using one of a scattering coefficient and an attenuation slope of the region of interest, said ultrasound diagnostic equipment comprising:

first ultrasound radiation and receipt means adapted to contact a body surface over the organ, for radiating an ultrasound beam to blood flowing inside a blood vessel or heart close to the region of interest and receiving ultrasound waves scattered from the blood; scattering power calculation means, connected to said first ultrasound radiation and receipt means, for calculating a Doppler signal power from said received ultrasound waves; and cumulative attenuation slope calculation means, connected to said scattering power calculation means, for calculating a cumulative attenuation slope based on the Doppler signal power calculated by said scattering power calculation means.

2. Ultrasound diagnostic equipment according to claim 1, wherein said ultrasound diagnostic equipment further comprises a coefficient calculation unit, connected to said cumulative attenuation slope calculation means, for calculating an average attenuation slope of the region of interest by using a plurality of cumulative attenuation slopes calculated by said cumulative attenuation slope calculation means.

3. Ultrasound diagnostic equipment according to claim 1, wherein said ultrasound diagnostic equipment further comprises:

scattering coefficient calculation means for calculating a scattering coefficient of the region of interest using the cumulative attenuation slope of the blood close to the region of interest; and second ultrasound radiation and receipt means connected to said scattering coefficient calculation means for calculating a scattering coefficient of the region of interest by using said calculated cumulative attenuation slope of the blood close to said region of interest and contacting said body surface over the organ, for radiating an ultrasound beam to the region of interest and receiving an ultrasound wave scattered from the region of interest.

4. Ultrasound diagnostic equipment according to claim 3, wherein said second ultrasound radiation and receipt means comprises:

an ultrasound probe, contacted to the body surface of the organ, for radiating an ultrasound beam to an optional portion in the organ and receiving an ultrasound wave scattered from said optional portion;

a transmitting amplifier, connected to said ultrasound probe, for driving said ultrasound probe; and a receiving amplifier, connected to said ultrasound probe, for amplifying the ultrasound wave signals received by said ultrasound probe.

5. Ultrasound diagnostic equipment according to claim 4, wherein said ultrasound diagnostic equipment further comprises:
a B-mode receiving circuit, connected to said receiving amplifier, for generating a B-mode image by luminance signals corresponding to signal strength of an output of said receiving amplifier.

6. Ultrasound diagnostic equipment according to claim 3, wherein said scattering coefficient calculation means comprises:
a scattering spectrum calculation unit;
a read only memory; and
a coefficient calculation unit connected to said scattering spectrum calculation unit and said read only memory.

7. Ultrasound diagnostic equipment according to claim 6, wherein said scattering spectrum calculation unit comprises:
an A/D converter, connected to said receiving amplifier, for converting an output signal of said receiving amplifier into a digital signal;
an operation circuit, connected to said A/D converter, for performing a high speed operation of a fast Fourier transform of an output signal of said A/D converter;
a power operation circuit, connected to said operation circuit, for calculating a real component and an imaginary component of said fast Fourier transform; and
an accumulator, connected to said power operation circuit, for adding a power spectrum of a scanning line in the region of interest.

8. Ultrasound diagnostic equipment according to claim 6, wherein said scattering spectrum calculation unit comprises:
a logarithmic amplifier, connected to said receiving amplifier, for amplifying the output signal of said receiving amplifier as a logarithmic compression;
an A/D converter, connected to said logarithmic amplifier, for converting an output signal of said logarithmic amplifier into a digital signal;
an inverse logarithmic circuit, connected to said A/D converter, for converting an output signal of said A/D converter into a primary antilogarithm;
an arithmetic circuit, connected to said inverse logarithmic circuit, for performing a high speed operation of a fast Fourier transform on an output signal of said inverse logarithmic circuit;
a power calculation circuit, connected to said arithmetic circuit, for calculating the sum of a square of a real component and a square of an imaginary component of the Fourier spectrum; and
an accumulator, connected to said power calculation circuit, for adding a power spectrum of a scanning line in the region of interest.

9. Ultrasound diagnostic equipment according to claim 1, wherein said first ultrasound radiation and receipt means comprises:
an ultrasound probe, adapted to contact a body surface over the organ, for radiating an ultrasound beam to an optional portion in the organ and receiving ultrasound waves scattered from the optional portion;
a transmitting amplifier, connected to said ultrasound probe, for driving said ultrasound probe; and
a receiving amplifier, connected to said ultrasound probe, for amplifying the ultrasound waves received by said ultrasound probe.

10. Ultrasound diagnostic equipment according to claim 1, wherein said scattering power calculation means comprises:
a Doppler signal calculation circuit, connected to said receiving amplifier, for calculating a Doppler signal of said receiving amplifier in a sample volume;
a power calculation circuit, connected to said Doppler signal calculation circuit, for calculating a power of the Doppler signal and calculating a sum of a square and averaging in time between and imaginary component and a real component of the Doppler signal; and
an A/D converter, connected to said power calculation circuit, for converting the power of the Doppler signal into a digital signal.

11. Ultrasound diagnostic equipment according to claim 1, wherein said cumulative attenuation slope calculation unit comprises a read only memory, connected to said scattering power calculation means, wherein scattering characteristics of said ultrasound beam, transmitting-receiving characteristics, and a power transfer function including frequency characteristics of said equipment are stored in said read only memory.

12. Ultrasound diagnostic equipment according to claim 1, wherein said ultrasound diagnostic equipment further comprises:
a coefficient calculation unit, connected to said cumulative attenuation slope calculation means, for calculating an average attenuation slope of an existing section among a plurality of blood positions based on the cumulative attenuation coefficients corresponding to blood positions calculated by said cumulative attenuation slope calculation means.

13. Ultrasound diagnostic equipment according to claim 12, wherein said coefficient calculation means calculates a scattering coefficient and an attenuation slope of the region of interest based on a calculated power spectrum of a reflected wave and the cumulative attenuation slope.

14. Ultrasound diagnostic equipment for diagnosing a region of interest of an organ by using a scattering coefficient and an attenuation slope of the region of interest, said ultrasound diagnostic equipment comprising:
an ultrasound probe, contacted to a body surface over the organ, for radiating an ultrasound beam to an optional portion in the organ and receiving an ultrasound wave scattered from said optional portion;
a transmitting amplifier, connected to said ultrasound probe, for driving said ultrasound probe;
a receiving amplifier, connected to said ultrasound probe, for amplifying the ultrasound wave signals received by said ultrasound probe;
a timing control unit, connected to said transmitting amplifier, for supplying pulse shape electric signals to said transmitting amplifier;
a B-mode receiving circuit, connected to said receiving amplifier, for generating a B-mode image by luminance signals corresponding to signal strength of an output of said receiving amplifier;
a scattering spectrum calculation unit, connected to said receiving amplifier, for calculating a scattering spectrum of said region of interest by using the output signals of said receiving amplifier;
a scattering power calculation unit, connected to said receiving amplifier and said timing control unit, for calculating an ultrasound scattering wave power scattered from the blood close to the region of interest;

a cumulative attenuation slope calculation unit, connected to said scattering power calculation unit and said timing control unit, for calculating a cumulative attenuation slope based on the ultrasound scattering wave power calculated by said scattering power calculation unit and said timing signal output from said timing control unit;

a read only memory, connected to said timing control unit, for reading out various data in response to addresses from said timing control unit;

a coefficient calculation unit, connected to said scattering spectrum calculation unit, said cumulative attenuation slope calculation unit and said read only memory, for calculating a scattering coefficient and an attenuation slope of the region of interest; and a display, connected to said B-mode receiving circuit and said coefficient calculation unit, for displaying a B-mode image and an image defined by the scattering coefficient and the attenuation slope of the region of interest.

15. Ultrasound diagnostic equipment according to claim 14, wherein said scattering spectrum calculation unit comprises:

an A/D converter, connected to said receiving amplifier, for converting an output signal of said receiving amplifier into a digital signal;

an arithmetic circuit, connected to said A/D converter, for performing a high speed operation of a fast Fourier transform of an output signal of said A/D converter;

a power operation circuit, connected to said arithmetic circuit, for calculating a real component and an imaginary component of the fast Fourier transform; and an accumulator, connected to said power operation circuit, for adding a power spectrum of a scanning line in the region of interest.

16. Ultrasound diagnostic equipment according to claim 14, wherein said scattering spectrum calculation unit comprises:

a logarithmic amplifier, connected to said receiving amplifier, for amplifying the output signal of said receiving amplifier as a logarithmic compression;

an A/D converter, connected to said logarithmic amplifier, for converting an output signal of said logarithmic amplifier into a digital signal;

an inverse logarithmic circuit, connected to said A/D converter, for converting an output signal of said A/D converter to a primary antilogarithm;

an operation circuit, connected to said inverse logarithmic circuit, for performing a high speed operation of a fast Fourier transform of an output signal of said inverse logarithmic circuit;

a power operation circuit, connected to said operation circuit, for calculating a real component and an imaginary component of the fast Fourier transform; and an accumulator, connected to said power operation circuit, for adding a power spectrum of a scanning line in the region of interest.

17. Ultrasound diagnostic equipment according to claim 14, wherein said scattering power calculation unit comprises:

a Doppler signal calculation circuit, connected to said receiving amplifier and said timing control unit, for calculating a Doppler signal of said receiving amplifier in a sample volume by the timing signal from said timing control unit;

a power calculation circuit, connected to said Doppler signal calculation circuit, for calculating a power of the Doppler signal by calculating a sum of a square and averaging in time between an imaginary component and a real component of the Doppler signal; and an A/D converter, connected to said power calculation circuit, for converting the power of the Doppler signal into a digital signal.

18. Ultrasound diagnostic equipment according to claim 14, wherein said cumulative attenuation slope calculation unit comprises a read only memory, connected to said scattering power calculation unit and said timing control unit, wherein scattering characteristics of said ultrasound beam, transmitting-receiving characteristics, and a power transfer function including frequency characteristics of said equipment are stored in said read only memory.

* * * * *

UNITED STATES PATENT AND TRADEMARK OFFICE
CERTIFICATE OF CORRECTION

PATENT NO.  : 5,095,909
DATED       : MARCH 17, 1992
INVENTOR(S) : KIYOSHI NAKAYAMA ET AL.

It is certified that error appears in the above-identified patent and that said Letters Patent is hereby corrected as shown below:

```
Col.  2, line 62, "connected the" should be --connected
                   to the--.

Col.  3, line  1, "a" should be deleted;
         line 53, "memory. diffraction" should be --memory,
                   diffraction--.

Col.  4, line 44, "a" should be --an--.

Col.  6, line  5, "6c" should be --6c is an--.

Col.  7, line 48, "commulative" should be --cumulative--.

Col. 12, line 49, "and" should be deleted.
```

Signed and Sealed this

Tenth Day of August, 1993

Attest:

MICHAEL K. KIRK

Attesting Officer

Acting Commissioner of Patents and Trademarks